US010800662B1

(12) United States Patent
Lew et al.

(10) Patent No.: US 10,800,662 B1
(45) Date of Patent: Oct. 13, 2020

(54) METHOD FOR PREPARING ZEOLITE SSZ-55

(71) Applicant: CHEVRON U.S.A. INC., San Ramon, CA (US)

(72) Inventors: Christopher Michael Lew, Alameda, CA (US); Dan Xie, El Cerrito, CA (US); Kurt Owen Jensen, Richmond, CA (US); Saleh Ali Elomari, Fairfield, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 0 days.

(21) Appl. No.: 16/822,168

(22) Filed: Mar. 18, 2020

(51) Int. Cl.
*C01B 39/48* (2006.01)
*B01J 29/70* (2006.01)
*B01J 29/74* (2006.01)
*C07C 5/22* (2006.01)

(52) U.S. Cl.
CPC .............. *C01B 39/48* (2013.01); *B01J 29/74* (2013.01); *C07C 5/222* (2013.01); *C01P 2002/72* (2013.01); *C07C 2529/068* (2013.01)

(58) Field of Classification Search
CPC . C01B 39/48; B01J 29/70; B01J 29/74; C01P 2002/72
See application file for complete search history.

(56) References Cited

U.S. PATENT DOCUMENTS

| 6,475,463 | B1 | 11/2002 | Elomari et al. |
| 6,632,416 | B2 | 10/2003 | Elomari |
| 6,632,417 | B2 * | 10/2003 | Elomari ................ B01J 29/40 423/706 |

OTHER PUBLICATIONS

Wu et al, "Synthesis and Structure Determination by ZEFSAII of SSZ-55: A New High-Silica, Large-Pore Zeolite", J. Phys. Chem. B 2002, 264-270 (Year: 2002).*
Zones et al, "The flouride based route to all-silica molecular sieves: a strategy for synthesis of new materials based upon close-packing of guest-host products", C.R.Chimie 8 (2005) 267-282 (Year: 2005).*
M.G. Wu, M.W. Deem, S.A. Elomari, R.C. Medrud, S.I. Zones, T. Maesen, C. Kibby, C-Y. Chen and I.Y. Chan "Synthesis and Structure Determination by ZEFSAII of SSZ-55: A New High-Silica, Large-Pore Zeolite" J. Phys. Chem. B 2002, 106, 264-270.
A. Burton, D.J. Darton, M.E. Davis, S-J. Hwang, R.E. Morris, I. Ogino and S.I. Zones "Structure-Directing Agent Location and Non-Centrosymmetric Structure of Fluoride-Containing Zeolite SSZ-55" J. Phys. Chem. B 2006, 110, 5273-5278.

* cited by examiner

*Primary Examiner* — David M Brunsman

(57) ABSTRACT

A method is provided for synthesizing a molecular sieve having the framework structure of SSZ-55 using [(1-phenyl)cyclopentylmethyl]trimethylammonium cations as a structure directing agent.

14 Claims, 2 Drawing Sheets

METHOD FOR PREPARING ZEOLITE SSZ-55

FIELD

This disclosure relates to the synthesis of zeolite SSZ-55.

BACKGROUND

Molecular sieves are a commercially important class of materials that have distinct crystal structures with defined pore structures that are shown by distinct X-ray diffraction (XRD) patterns and have specific chemical compositions. The crystal structure defines cavities and pores that are characteristic of the specific type of molecular sieve.

Molecular sieves are classified by the Structure Commission of the International Zeolite Association according to the rules of the IUPAC Commission on Zeolite Nomenclature. According to this classification, framework type zeolites and other crystalline microporous molecular sieves, for which a structure has been established, are assigned a three-letter code and are described in the "Atlas of Zeolite Framework Types," Sixth Revised Edition, Elsevier (2007).

One known molecular sieve for which a structure has been established is the material designated as ATS, which is a molecular sieve having one-dimensional pores circumscribed by 12 T-atom rings. Molecular sieves with the ATS framework type include AlPO-36, FAPO-36, MAPO-36, ZnAPO and SSZ-55.

U.S. Pat. No. 6,475,463 discloses zeolite SSZ-55 and its synthesis using N,N,N-trimethyl-[1-(3-fluorophenyl)cyclopentyl] methyl ammonium cations, N,N,N-trimethyl-(1-phenylcyclobutyl)methyl ammonium cations, or N-cyclohexyl-N-(2-methylpropyl)pyrrolidinium cations as a structure directing agent.

According to the present disclosure, it has now been found that SSZ-55 can be synthesized using [1-(phenyl)cyclopentylmethyl]trimethylammonium cations as a structure directing agent.

SUMMARY

In one aspect, there is provided a method of synthesizing a molecular sieve having the structure of SSZ-55, the method comprising: (a) providing a reaction mixture comprising: (1) a source of an oxide of a tetravalent element (T); (2) optionally, a source of an oxide of a trivalent element (X); (3) a structure directing agent (Q) comprising [(1-phenyl)cyclopentylmethyl]trimethylammonium cations; (4) a source of fluoride ions; and (5) water; and (b) subjecting the reaction mixture to crystallization conditions sufficient to form crystals of the molecular sieve.

In another aspect, there is provided a molecular sieve having the structure of SSZ-55 and, in its as-synthesized form, comprising [(1-phenyl)cyclopentylmethyl]trimethylammonium cations in its pores.

The molecular sieve can have, in its as-synthesized and anhydrous form, a chemical composition comprising the following molar relationship:

|  | Useful | Typical |
|---|---|---|
| $TO_2/X_2O_3$ | ≥20 | ≥25 |
| $Q/TO_2$ | >0 to 1.0 | >0 to 1.0 | wherein T is a tetravalent element; X is a trivalent element; and Q comprises [(1-phenyl)cyclopentylmethyl] trimethylammonium cations.

DETAILED DESCRIPTION

Definitions

Figure 1:
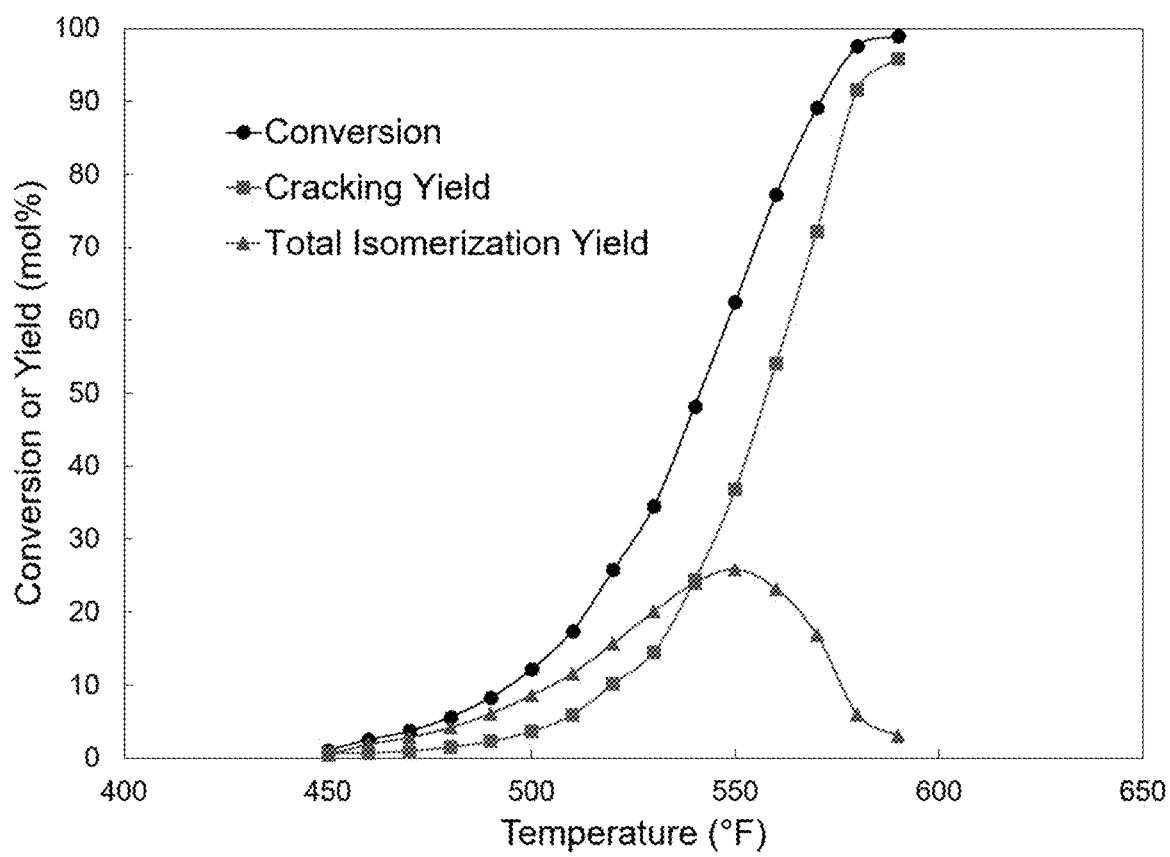
FIG. 1 is a graph illustrating the relationship between n-decane conversion and reaction temperature over the Pt/Al-SSZ-55 catalyst of Example 4.

As used herein, the term "molecular sieve" is used synonymously with the term "zeolite" or "microporous crystalline material".

The term "as-synthesized" refers to a molecular sieve in its form after crystallization, prior to removal of the structure directing agent.

The term "anhydrous" refers to a molecular sieve substantially devoid of both physically adsorbed and chemically adsorbed water.

The term "silicate" refers to a molecular sieve including silicon oxide within its framework structure. It is a general term including, for example, pure silicate (i.e., absent other detectable metal oxides with the framework), aluminosilicate, borosilicate, ferrosilicate, germanosilicate, or titanosilicate structures.

The term "aluminosilicate" refers to a molecular sieve including silicon and aluminum oxides within its framework structure.

The term "germanosilicate" refers to a molecular sieve including germanium and silicon oxides within its framework structure.

As used herein, the numbering scheme for the Periodic Table Groups is as disclosed in *Chem. Eng. News* 1985, 63(5), 26-27.

Synthesis of SSZ-55

In general, a molecular sieve having the framework structure of SSZ-55 can be synthesized by: (a) providing a reaction mixture comprising: (1) a source of an oxide of a tetravalent element (T); (2) optionally, a source of an oxide of a trivalent element (X); (3) a structure directing agent (Q) comprising [(1-phenyl)cyclopentylmethyl]trimethylammonium cations; (4) a source of fluoride ions; and (5) water; and (b) subjecting the reaction mixture to crystallization conditions sufficient to form crystals of the molecular sieve.

The reaction mixture can have a composition, in terms of molar ratios, as identified in Table 1 below:

TABLE 1

| Reactants | Useful | Typical |
|---|---|---|
| $TO_2/X_2O_3$ | ≥20 | ≥25 |
| $Q/TO_2$ | 0.10 to 1.00 | 0.15 to 0.60 |
| $F/TO_2$ | 0.10 to 1.00 | 0.15 to 0.60 |
| $H_2O/TO_2$ | 2 to 25 | 5 to 20 | wherein compositional variables T, X and Q are as described herein above.

Suitable sources of the tetravalent element (T) depend on the element T selected (e.g., silicon, germanium, titanium, and zirconium). In aspects where T is or comprises silicon, suitable sources of silicon include fumed silica, colloidal silica, precipitated silica, alkali metal silicates, and tetraalkyl orthosilicates. In aspects where T is or comprises germanium, suitable sources of germanium include germanium oxide and germanium alkoxides (e.g., germanium ethoxide).

If present, suitable sources of the trivalent element (X) depend on the element X that is selected (e.g., boron, aluminum, gallium, and iron). In aspects where X is aluminum, suitable sources of aluminum include hydrated alumina, aluminum hydroxide, alkali metal aluminates, aluminum alkoxides, and water-soluble aluminum salts (e.g., aluminum nitrate).

Suitable sources of fluoride ions include hydrogen fluoride, ammonium fluoride, and ammonium hydrogen difluoride.

The structure directing agent (Q) comprises [(1-phenyl)cyclopentylmethyl]trimethylammonium cations, represented by the following structure (1):

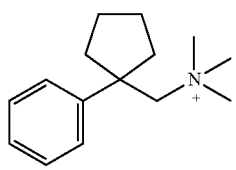

(1)

Suitable sources of Q are the hydroxides and/or other salts of the quaternary ammonium compound.

The reaction mixture may also contain seeds of a molecular sieve material, such as SSZ-55, such that a weight ratio of seeds/$TO_2$ in the reaction mixture can be from 0.001 to 0.3 (e.g., 0.001 to 0.2, 0.001 to 0.1, 0.01 to 0.3, 0.01 to 0.2, 0.01 to 0.1, 0.01 to 0.08, 0.03 to 0.3, 0.03 to 0.2, 0.03 to 0.1, or 0.03 to 0.08). Seeding can be advantageous in decreasing the amount of time necessary for complete crystallization to occur. In addition, seeding can lead to an increased purity of the product obtained by promoting the nucleation and/or formation of SSZ-55 over any undesired phases.

The reaction mixture components can be supplied by more than one source. Also, two or more reaction components can be provided by one source.

The reaction mixture can be prepared either batch wise or continuously. Crystal size, morphology and crystallization time of the molecular sieve described herein can vary with the nature of the reaction mixture and the crystallization conditions.

Crystallization of the molecular sieve from the above reaction mixture can be carried out under either static, tumbled or stirred conditions in a suitable reactor vessel, such as for example polypropylene jars or Teflon-lined or stainless-steel autoclaves, at a temperature of from 125° C. to 200° C. for a time sufficient for crystallization to occur at the temperature used (e.g., from about 1 day to about 14 days, or from about 2 days to about 10 days). Crystallization is usually conducted in an autoclave so that the reaction mixture is subject to autogenous pressure.

Once the molecular sieve crystals have formed, the solid product can be separated from the reaction mixture by standard mechanical separation techniques such as centrifugation or filtration. The crystals are water-washed and then dried to obtain the as-synthesized molecular sieve crystals. The drying step can be performed at an elevated temperature (e.g., 75° C. to 150° C.) for several hours (e.g., about 4 to 24 hours). The drying step can be performed under vacuum or at atmospheric pressure.

As a result of the crystallization process, the recovered crystalline molecular sieve product contains within its pores at least a portion of the structure directing agent used in the synthesis.

The as-synthesized molecular sieve may be subjected to treatment to remove part or all of the structure directing agent used in its synthesis. Removal of the structure directing agent may be carried out by thermal treatment (e.g., calcination) in which the as-synthesized molecular sieve is heated at a temperature sufficient to remove part or all of the structure directing agent. While sub-atmospheric pressure may be used for the thermal treatment, atmospheric pressure is desired for reasons of convenience. The thermal treatment may be performed at a temperature at least 370° C. for at least a minute and generally not longer than 20 hours (e.g., from 1 to 12 hours). The thermal treatment can be performed at a temperature of up to 925° C. For example, the thermal treatment may be conducted at a temperature of 400° C. to 600° C. in the presence of an oxygen-containing gas. Additionally or alternatively, the structure directing agent may be removed by treatment with ozone.

The present synthesis of SSZ-55 can be accomplished in the absence of Group 1 and/or Group 2 metal cations, thereby obviating the need for ion-exchange of the product after thermal treatment to remove any occluded structure directing agent. To the extent desired and depending on the $TO_2/X_2O_3$ molar ratio of the material, any cations in the as-synthesized molecular sieve can be replaced in accordance with techniques well known in the art by ion exchange with other cations. Preferred replacing cations include metal ions (e.g., rare earth metals and metals of Groups 2 to 15 of the Periodic Table), hydrogen ions, hydrogen precursor ions (e.g., ammonium ions), and combinations thereof.

Characterization of the Molecular Sieve

In its as-synthesized and anhydrous form, molecular sieve SSZ-55 prepared as described herein can have a chemical composition comprising the following molar relationship as set forth in Table 2:

TABLE 2

|  | Useful | Preferred |
|---|---|---|
| $TO_2/X_2O_3$ | ≥20 | ≥25 |
| $Q/TO_2$ | >0 to 1.0 | >0 to 1.0 | wherein T is a tetravalent element; X is a trivalent element; and Q comprises [(1-phenyl)cyclopentylmethyl]trimethylammonium cations.

In some aspects, the molecular sieve may be a pure silicate, an aluminosilicate, or a germanosilicate.

As taught by U.S. Pat. No. 6,475,463, zeolite SSZ-55 has a powder X-ray diffraction pattern which, in its as-synthesized form, includes at least the peaks set forth in Table 3 below and which, in its calcined form, includes at least the peaks set forth in Table 4.

TABLE 3

Characteristic Peaks for As-Synthesized SSZ-55

| 2-Theta [°][a] | d-spacing [Å] | Relative Intensity[b] |
|---|---|---|
| 7.94 | 11.13 | S |
| 15.98 | 5.54 | M |
| 16.60 | 5.33 | S |
| 19.24 | 4.61 | M |
| 20.97 | 4.23 | VS |

TABLE 3-continued

Characteristic Peaks for As-Synthesized SSZ-55

| 2-Theta [°][a] | d-spacing [Å] | Relative Intensity[b] |
|---|---|---|
| 21.93 | 4.05 | M |
| 22.48 | 3.95 | VS |
| 23.68 | 3.75 | M |
| 27.54 | 3.24 | M |
| 35.08 | 2.56 | W |

[a]±0.2
[b]The powder XRD patterns provided are based on a relative intensity scale in which the strongest line in the XRD pattern is assigned a value of 100: W (weak) is <20; M (medium) is ≥20 to <40; S (strong) is ≥40 to <60; and VS (very strong) is ≥60.

TABLE 4

Characteristic Peaks for Calcined SSZ-55

| 2-Theta [°][a] | d-spacing [Å] | Relative Intensity |
|---|---|---|
| 7.94 | 11.13 | VS |
| 13.60 | 6.51 | W |
| 16.67 | 5.31 | M |
| 19.31 | 4.59 | W-M |
| 20.92 | 4.24 | W-M |
| 22.00 | 4.04 | W |
| 22.56 | 3.94 | W-M |
| 27.46 | 3.24 | W |
| 28.73 | 3.10 | W |
| 32.32 | 2.77 | W |

[a]±0.2

The powder X-ray diffraction patterns presented herein were collected by standard techniques. The radiation was CuKα radiation. The peak heights and the positions, as a function of 2θ where θ is the Bragg angle, were read from the relative intensities of the peaks (adjusting for background), and d, the interplanar spacing corresponding to the recorded lines, can be calculated.

Minor variations in the diffraction pattern can result from variations in the mole ratios of the framework species of the particular sample due to changes in lattice constants. In addition, sufficiently small crystals will affect the shape and intensity of peaks, leading to significant peak broadening. Minor variations in the diffraction pattern can also result from variations in the organic compound used in the preparation. Calcination can also cause minor shifts in the XRD pattern. Notwithstanding these minor perturbations, the basic crystal lattice structure remains unchanged.

EXAMPLES

The following illustrative examples are intended to be non-limiting.

Example 1

6.34 g of [(1-phenyl)cyclopentyl)methyl]trimethylammonium hydroxide solution (Q, 13.23 wt. % in water) was added to a Teflon liner. Then, 1.50 g of tetraethylorthosilicate (99%, TEOS) was added. The TEOS was hydrolyzed by stirring at room temperature overnight. The resulting ethanol was evaporated by gently blowing a stream of nitrogen over the top of the Teflon liner. Deionized water was re-added to adjust for the correct molar water ratio. Hydrofluoric acid (48%, HF) was added to the liner, and then 0.02 g SSZ-55 seeds were added to the liner. The final molar ratio of the resulting gel was as follows:

$1SiO_2:0.5Q:0.5HF:3H_2O$

The liner was sealed and placed in an autoclave. The autoclave was heated at 160° C. for 7 days with rotation (43 rpm). The product was separated from the reaction mixture by centrifugation, thoroughly washed with excess deionized water and methanol and dried in an oven at 95° C.

The resulting product was analyzed by powder XRD. Powder XRD pattern showed the product to be pure SSZ-55.

Examples 2-8

A series of gels were prepared in a manner similar to Example 1, but having the composition, in terms of molar ratios, indicated in Table 5. Where present, aluminum isopropoxide was the source of aluminum, and germanium oxide was the source of germanium. Each gel had a seeds-to-$SiO_2$ weight ratio of 0.05.

The products were separated from their reaction mixtures by centrifugation, washed with deionized water and dried. Analysis of the XRD patterns showed each of the products to be pure SSZ-55.

Some materials prepared in the examples were further characterized in terms of porosity and/or acidity. The results are presented in Table 5.

Micropore volume ($V_{micro}$) was measured with nitrogen physisorption, and the data analyzed by the t-plot method, according to the method of B.C Lippens et al. (J. Catal. 1965, 4, 319-323). Calcination of as-synthesized materials was carried out in an air oven at 550° C. for 5 hours using a heating rate of 1° C./min.

Acid site density was determined by n-propylamine temperature-programmed desorption (TPD) adapted from the published descriptions by T. J. Gricus Kofke et al. (J. Catal. 1988, 114, 34-45); T. J. Gricus Kofke et al. (J. Catal. 1989, 115, 265-272); and J. G. Tittensor et al. (J. Catal. 1992, 138, 714-720). A sample was pre-treated at 400° C.-500° C. for 1 hour in flowing dry $H_2$. The dehydrated sample was then cooled down to 120° C. in flowing dry helium and held at 120° C. for 30 minutes in a flowing helium saturated with n-propylamine for adsorption. The n-propylamine-saturated sample was then heated up to 500° C. at a rate of 10° C./minute in flowing dry helium. Acid site density was calculated based on the weight loss vs. temperature by thermogravimetric analysis (TGA) and effluent $NH_3$ and propene by mass spectrometry.

TABLE 5

| | Reaction Mixture | | | | Product | |
|---|---|---|---|---|---|---|
| | $SiO_2/Al_2O_3$ | Si/Ge | $Q/SiO_2$ | $F/SiO_2$ | $H_2O/SiO_2$ | $V_{micro}$ [cm³/g] | Acid Site Density [μmol/g] |
| Ex. 2 | 0 | 0 | 0.5 | 0.5 | 7 | 0.1934 | |
| Ex. 3 | 0 | 0 | 0.5 | 0.5 | 15 | | |
| Ex. 4 | 25 | 0 | 0.5 | 0.5 | 7 | 0.1832 | 596 |
| Ex. 5 | 50 | 0 | 0.5 | 0.5 | 7 | 0.1835 | 428 |
| Ex. 6 | 100 | 0 | 0.5 | 0.5 | 7 | 0.1699 | 240 |
| Ex. 7 | 0 | 6 | 0.5 | 0.5 | 10 | 0.1880 | |
| Ex. 8 | 0 | 10 | 0.5 | 0.5 | 10 | | |

Example 9

Hydroconversion of n-Decane

Aluminosilicate materials (Al-SSZ-55) obtained in Examples 4-5 were evaluated for catalytic activity in the n-decane hydroconversion reaction. Before catalytic testing, the materials were impregnated with 0.5 wt. % Pt using an aqueous solution of $Pt(NH_3)_4(NO_3)_2$. The recovered Pt/Al-SSZ-55 molecular sieve was washed with deionized water, dried at 95° C. and then calcined to 300° C. for 3 hours. The calcined Pt/Al-SSZ-55 catalyst was then pelletized, crushed, and sieved to 20-40 mesh.

0.5 g of Pt/Al-SSZ-55 catalyst was loaded in the center of a ¼ inch OD stainless steel reactor tube with alundum loaded upstream of the catalyst for preheating the feed (a total pressure of 1200 psig; a down-flow hydrogen rate of 160 mL/min when measured at 1 atmosphere pressure and 25° C.; and a down-flow liquid feed rate of 1 mL/hour). All materials were first reduced in flowing hydrogen at about 315° C. for 1 hour. Products were analyzed by on-line capillary gas chromatography (GC) once every 60 minutes. Raw data from the GC was collected by an automated data collection/processing system and hydrocarbon conversions were calculated from the raw data. Conversion is defined as the amount n-decane reacted to produce other products (including iso-C10). Yields are expressed as mole percent of products other than n-decane and include iso-C10 isomers as a yield product.

Figure 2:
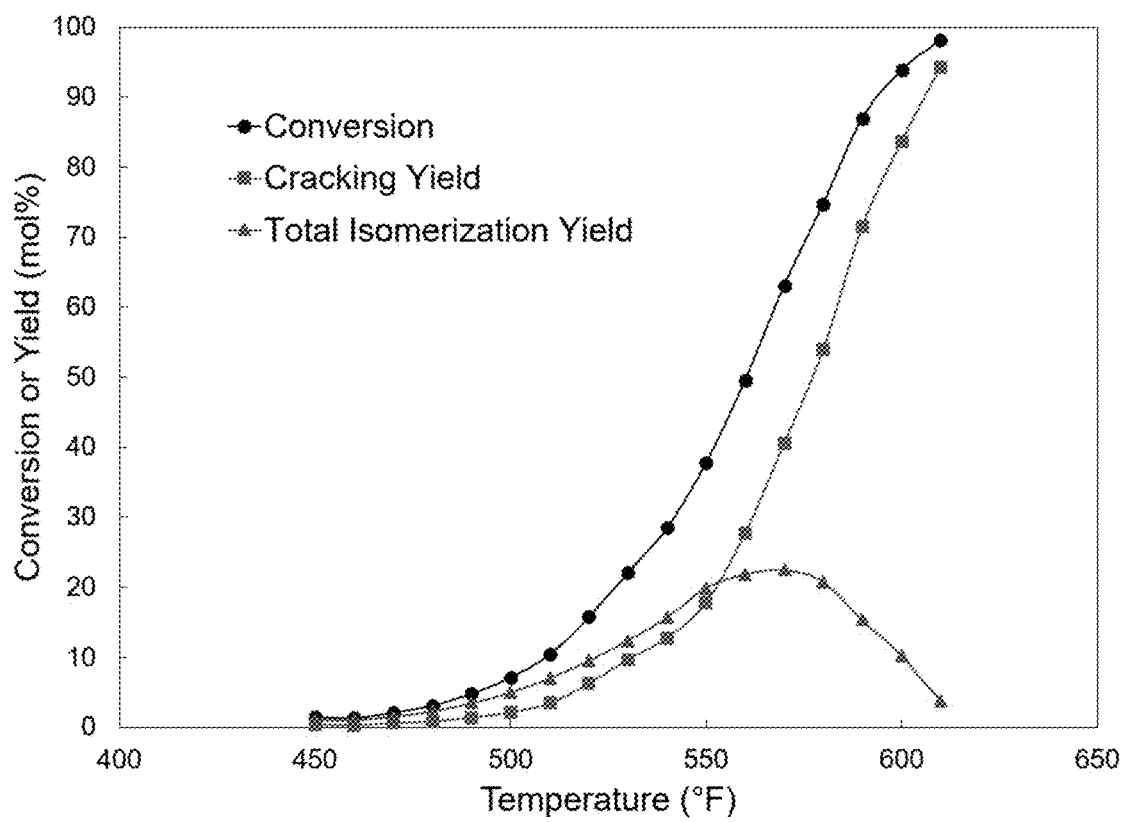
FIG. 2 is a graph illustrating the relationship between n-decane conversion and reaction temperature over the Pt/Al-SSZ-55 catalyst of Example 5.

FIG. 1 and FIG. 2 are graphs illustrating the relationship between n-decane conversion and reaction temperature over the Pt/Al-SSZ-55 catalyst of Example 4 and Example 5, respectively.

The invention claimed is:

1. A method of synthesizing a molecular sieve having the structure of SSZ-55, the method comprising:
   (a) providing a reaction mixture comprising:
      (1) a source of an oxide of a tetravalent element (T);
      (2) optionally, a source of an oxide of a trivalent element (X);
      (3) a structure directing agent (Q) comprising (1-phenyl)cyclopentylmethyl]trimethylammonium cations;
      (4) a source of fluoride ions; and
      (5) water; and
   (b) subjecting the reaction mixture to crystallization conditions sufficient to form crystals of the molecular sieve.

2. The method of claim 1, wherein the reaction mixture has a composition, in terms of molar ratios, as follows:

| | |
|---|---|
| $TO_2/X_2O_3$ | ≥20 |
| $Q/TO_2$ | 0.10 to 1.00 |
| $F/TO_2$ | 0.10 to 1.00 |
| $H_2O/TO_2$ | 2 to 25. |

3. The method of claim 1, wherein the reaction mixture has a composition, in terms of molar ratios, as follows:

| | |
|---|---|
| $SiO_2/X_2O_3$ | ≥25 |
| $Q/SiO_2$ | 0.15 to 0.60 |
| $F/SiO_2$ | 0.15 to 0.60 |
| $H_2O/SiO_2$ | 5 to 20. |

4. The method of claim 1, wherein the tetravalent element T comprises one or more of silicon and germanium.

5. The method of claim 1, wherein the tetravalent element T comprises silicon and the trivalent element X comprises aluminum.

6. The method of claim 1, wherein the reaction mixture also contains seeds.

7. The method of claim 6, wherein the seeds are present in an amount such that a weight ratio of seeds to oxide of tetravalent element (T) in the reaction mixture is in a range of from 0.001 to 0.3.

8. The method of claim 6, wherein the seeds comprise a molecular sieve material having the structure of SSZ-55.

9. The method of claim 1, wherein the crystallization conditions include a temperature of from 125° C. to 200° C.

10. A molecular sieve having the structure of SSZ-55 and, in its as-synthesized form, comprising (1-phenyl)cyclopentylmethyl]trimethylammonium cations in its pores.

11. The molecular sieve of claim 10, having a molar ratio of $TO_2/X_2O_3$ of at least 20, wherein T is tetravalent element and X is a trivalent element.

12. The molecular sieve of claim 11, wherein the molar ratio of $TO_2/X_2O_3$ is at least 25.

13. The molecular sieve of claim 11, wherein the tetravalent element T comprises one or more of silicon and germanium.

14. The molecular sieve of claim 11, wherein the tetravalent element T comprises silicon and the trivalent element X comprises aluminum.

\* \* \* \* \*